United States Patent
Schiller et al.

(10) Patent No.: US 8,636,702 B2
(45) Date of Patent: Jan. 28, 2014

(54) MAGNIFYING COLLAPSED PLUNGER ROD

(75) Inventors: Eric Schiller, Westfield, NJ (US); Chee Leong Lum, Pequannock, NJ (US); Flora Felsovalyi, Oak Ridge, NJ (US)

(73) Assignee: Beckton Dickinson France, S.A.S., Le Pont-de-Claix (FR)

( * ) Notice: Subject to any disclaimer, the term of this patent is extended or adjusted under 35 U.S.C. 154(b) by 103 days.

(21) Appl. No.: 12/859,815

(22) Filed: Aug. 20, 2010

(65) Prior Publication Data

US 2011/0046560 A1     Feb. 24, 2011

Related U.S. Application Data

(60) Provisional application No. 61/235,848, filed on Aug. 21, 2009, provisional application No. 61/235,869, filed on Aug. 21, 2009, provisional application No. 61/235,817, filed on Aug. 21, 2009.

(51) Int. Cl.
*A61M 3/00* (2006.01)
*A61M 5/00* (2006.01)
*A61M 5/315* (2006.01)

(52) U.S. Cl.
USPC ........... 604/189; 604/181; 604/187; 604/218; 604/223; 604/228

(58) Field of Classification Search
USPC ......... 604/181, 187, 189, 207, 218, 223, 228, 604/233, 68
See application file for complete search history.

(56) References Cited

U.S. PATENT DOCUMENTS

| 330,621 A | 11/1885 | Reichardt |
| 622,848 A | 4/1899 | Geer |
| 1,008,078 A | 11/1911 | Schroeder |
| 1,512,294 A | 10/1924 | Marcy |
| 1,678,991 A * | 7/1928 | Marschalek ................ 604/220 |
| 1,715,771 A | 6/1929 | MacGregor |
| 1,737,857 A | 12/1929 | MacGregor |
| 1,971,687 A | 8/1934 | Kratz |
| 2,390,246 A | 12/1945 | Folkman |
| 2,461,481 A | 2/1949 | Roehr |
| 2,561,233 A | 7/1951 | Ryan et al. |
| 2,586,581 A | 2/1952 | Tschischeck |
| 2,630,804 A | 3/1953 | Mende |
| 2,646,042 A * | 7/1953 | Hu ................................ 604/38 |
| 2,671,450 A | 3/1954 | Dann |
| 2,672,142 A | 3/1954 | Melton |

(Continued)

FOREIGN PATENT DOCUMENTS

WO     9729798 A1     8/1997

*Primary Examiner* — Kevin C Sirmons
*Assistant Examiner* — Shefali Patel
(74) *Attorney, Agent, or Firm* — The Webb Law Firm

(57) ABSTRACT

A syringe assembly having a collapsible or pivotable plunger rod with magnification properties is provided. In a pre-use or packaged state, the plunger rod is positioned substantially parallel to a barrel of the syringe assembly resulting in the syringe assembly having a reduced length and a smaller packaging footprint. The smaller packaging footprint allows for reduced storage space of the syringe assembly. Upon removal from a packaging and/or a storage space, the plunger rod can be slid or pivoted toward a proximal end of the syringe barrel and locked into place such that the syringe assembly is ready for use. The plunger rod can be shaped to provide magnification to indicia of the syringe barrel and/or contents. Alternatively, a separate magnification member can be associated with the plunger rod and/or secured about the syringe barrel.

14 Claims, 13 Drawing Sheets

(56) References Cited

U.S. PATENT DOCUMENTS

| | | | |
|---|---|---|---|
| 2,672,868 | A | 3/1954 | Hickey |
| 2,673,562 | A | 3/1954 | Wadinger |
| 2,773,500 | A | 12/1956 | Young |
| 2,871,858 | A | 2/1959 | Dann et al. |
| 3,495,591 | A | 2/1970 | Wilson |
| 3,762,799 | A | 10/1973 | Shapiro |
| 4,011,868 | A | 3/1977 | Friend |
| 4,178,071 | A | 12/1979 | Asbell |
| 4,221,218 | A | 9/1980 | Pfleger |
| 4,475,915 | A | 10/1984 | Sloane |
| 4,518,387 | A | 5/1985 | Murphy et al. |
| 4,581,023 | A * | 4/1986 | Kuntz ............................ 604/234 |
| 4,743,234 | A * | 5/1988 | Leopoldi et al. ............... 604/187 |
| 4,832,696 | A | 5/1989 | Luther et al. |
| 4,850,973 | A | 7/1989 | Jordan et al. |
| D302,726 | S | 8/1989 | Schwöbel |
| 5,067,947 | A | 11/1991 | Volk et al. |
| 5,086,780 | A | 2/1992 | Schmitt |
| 5,098,382 | A | 3/1992 | Haber et al. |
| 5,135,507 | A | 8/1992 | Haber et al. |
| 5,176,657 | A | 1/1993 | Shields |
| 5,247,972 | A | 9/1993 | Tetreault |
| 5,377,725 | A | 1/1995 | Neff |
| D366,698 | S | 1/1996 | Stiehl et al. |
| 5,487,738 | A | 1/1996 | Sciulli |
| 5,498,243 | A | 3/1996 | Vallelunga et al. |
| 5,573,514 | A | 11/1996 | Stiehl et al. |
| 5,700,246 | A | 12/1997 | Stiehl et al. |
| 5,894,870 | A | 4/1999 | Maxwell |
| 6,001,082 | A | 12/1999 | Dair et al. |
| 6,210,359 | B1 | 4/2001 | Patel et al. |
| 6,656,161 | B2 | 12/2003 | Young et al. |
| 6,719,735 | B1 | 4/2004 | Gammon |
| 6,936,034 | B2 | 8/2005 | Watkins |
| 7,569,036 | B2 | 8/2009 | Domkowski et al. |
| 2005/0154354 | A1 | 7/2005 | Kawasaki et al. |
| 2006/0229568 | A1 | 10/2006 | Koopman |
| 2007/0088285 | A1 | 4/2007 | Sharp et al. |
| 2007/0219506 | A1* | 9/2007 | Andersson .................... 604/207 |
| 2009/0182284 | A1 | 7/2009 | Morgan |

* cited by examiner

MAGNIFYING COLLAPSED PLUNGER ROD

CROSS REFERENCE TO RELATED APPLICATIONS

This application claims benefit of U.S. Provisional Patent Application Nos. 61/235,848 entitled "Magnifying Collapsed Plunger Rod" filed Aug. 21, 2009; 61/235,869 entitled "Syringe Having a Collapsible Plunger Rod" filed Aug. 21, 2009; and 61/235,817 entitled "Syringe Assembly with Pivoting Plunger and Integral Tip Guard" filed Aug. 21, 2009, which are hereby incorporated by reference in their entirety.

BACKGROUND OF THE INVENTION

1. Field of the Invention

The present invention is directed to a syringe assembly having a collapsed plunger rod, and more particularly, to a syringe assembly having a collapsed plunger rod wherein the plunger rod has magnification properties to reduce medication errors. The present invention is also directed to a syringe assembly having a smaller packaging footprint allowing for reduced storage space.

2. Description of Related Art

Syringe assemblies, and in particular hypodermic syringes, are well known in the medical field for dispensing fluids, such as medication. A conventional syringe typically includes a syringe barrel with an opening at one end and a plunger mechanism disposed through the other end. The plunger typically includes a plunger rod extending through the barrel, with a plunger head or stopper at the end of the plunger rod within the barrel and with a finger flange at the other end of the plunger rod extending out of the barrel. In use, the plunger rod is retracted through the syringe barrel to fill the syringe barrel with a fluid, such as a medication, with the plunger rod extending out from the rear end of the syringe barrel. For delivery of the medication to a patient, the opening of the syringe barrel is adapted for fluid communication with a patient, such as through a hypodermic needle fitted at the front end of the syringe barrel or through a luer-type fitting extending from the front end of the syringe barrel for attachment with a fluid line of a patient. Upon depression of the plunger rod, the plunger rod and stopper travel through the syringe barrel, thereby forcing the contents of the syringe out through the opening at the front end for delivery to the patient. Such an operation is well known in the medical field, and medical practitioners have become well accustomed to the use of such common fluid delivery procedures through standard syringes.

Syringe assemblies having magnification members which are separately attached to the syringe barrel are also well known. U.S. Pat. No. 2,586,581 to Tschischeck discloses a magnifying attachment that fits around a syringe barrel. U.S. Pat. No. 4,178,071 to Asbell discloses a movable lens for viewing indicia lines that are visually accessible through a transparent region of a syringe body. The movable lens is carried by straps clasped to the exterior surface of tubing surrounding the syringe body. U.S. Pat. No. 4,743,234 to Leopoldi et al. discloses a syringe magnifier that is attached directly onto a syringe barrel.

Conventional syringes are well known to be used in connection with a vial of a medication, where the user draws the fluid into the syringe immediately prior to injection and delivery of the fluid to the patient. Oftentimes, hypodermic syringes may be packaged as "pre-filled" devices, wherein the syringe is pre-filled with medication prior to being packaged and delivered to the end user. In this manner, there is no need for the user to fill the device prior to injection, thereby saving time for the end user and maintaining consistent volumes for delivery.

Pre-filled syringes and pre-filled metered dose syringes are often filled with narcotics or other drugs at a production facility, packaged, and then shipped to a medical facility. Once at the facility, these syringes are often placed in controlled storage and/or locked cabinets to reduce theft of the syringes themselves and/or theft of the contents of these syringes. The space within these controlled storage locations is often limited, thus there is a need for a syringe assembly that has magnification properties wherein the magnification member is an integral component of the assembly such that the syringe assembly has a smaller packaging footprint to reduce the storage space required for containing this syringe. It is also desirable to produce syringes that are uniform in terms of an outer surface shape to allow for stacking of the syringes within the storage cabinet.

SUMMARY OF THE INVENTION

According to a first aspect, the invention is directed to a syringe assembly having a collapsed plunger rod wherein the plunger rod has magnification properties. The syringe barrel has a proximal end, a distal end, and a sidewall extending between the proximal end and the distal end. A stopper is located within the syringe barrel and a stopper adapter associated with the stopper. The syringe barrel, stopper, and stopper adapter define a longitudinal axis. A plunger rod is secured to the adapter and is configured for cooperation with the adapter to move from a collapsed pre-use position, where the plunger rod extends substantially parallel with the barrel sidewall and is capable of magnifying indicia, such as content identifying indicia associated with the barrel sidewall, to an expanded ready-to-use position where the plunger rod extends substantially in line with the longitudinal axis of the syringe barrel, stopper, and the stopper adapter. The plunger rod includes a first end and a second end and an attachment member located at the second end. This attachment member on the plunger rod cooperates with the stopper adapter to secure the plunger rod thereto in the expanded ready-to-use position. The syringe assembly can further include a flange located at the proximal end of the syringe barrel. This flange includes an opening in alignment with an opening in the stopper adapter through which the plunger rod extends. A magnification member is associated with the plunger rod for magnifying any indicia associated with the syringe barrel.

In operation, the plunger rod moves from the collapsed position to the expanded position through a pivoting motion of the second end of the plunger rod in a radial direction with respect to the syringe barrel, and through the application of a force to the plunger rod in a proximal direction toward the proximal end of the syringe barrel to axially slide the plunger rod through the openings in the flange and the stopper adapter to align the plunger rod along the longitudinal axis of the syringe barrel, stopper, and stopper adapter and to secure the attachment member on the second end of the plunger rod with the stopper adapter. The plunger rod can include a thumb press member located at the first end of the rod and is positioned above the proximal end of the syringe barrel and the flange.

According to one embodiment, the plunger rod can include magnification properties for magnifying any indicia associated with and/or located on the syringe barrel. One modification to this embodiment can include a plunger rod having two or more legs and wherein at least one of these legs includes magnification properties. According to another embodiment, a sleeve can be fitted about the syringe barrel. This sleeve can include a magnification lens incorporated therein.

According to another aspect, the invention is directed to a syringe assembly having magnification properties comprising a syringe barrel having a proximal end, a distal end, and a sidewall extending between the proximal end and the distal end. The sidewall can include indicia printed directly thereon or printed on a label secured to the sidewall. This indicia can include label information such as the drug name, concentration, expiration, and the like. The indicia can also include dosing information or barrel markings. A magnification member is associated with the plunger rod and the syringe barrel for magnifying this indicia. According to one embodiment, this magnification member comprises a collapsed plunger rod having at least a portion positioned adjacent the syringe barrel sidewall. According to one alternative design, the collapsed plunger rod can include two or more legs and at least one of the legs has magnification properties. According to an alternative embodiment, the magnification member can comprise a sleeve fitting about the syringe barrel wherein the sleeve includes a magnification lens incorporated therein. According to yet another alternative design, the plunger rod can be a pivoting plunger which pivots from a first position, in which the rod is adjacent to the syringe barrel, to a second position in which the plunger rod is in general axial alignment with the syringe barrel, and is further adapted for axial movement so as to cause the slidable movement of the plunger head through the syringe barrel. The pivoting plunger rod can include a tip guard integrally formed with a distal end thereof for protecting the distal end of the syringe assembly. The pivoting plunger can include a magnification member associated therewith for magnifying indicia associated with the syringe barrel.

DESCRIPTION OF THE PREFERRED EMBODIMENTS

Figure 1:
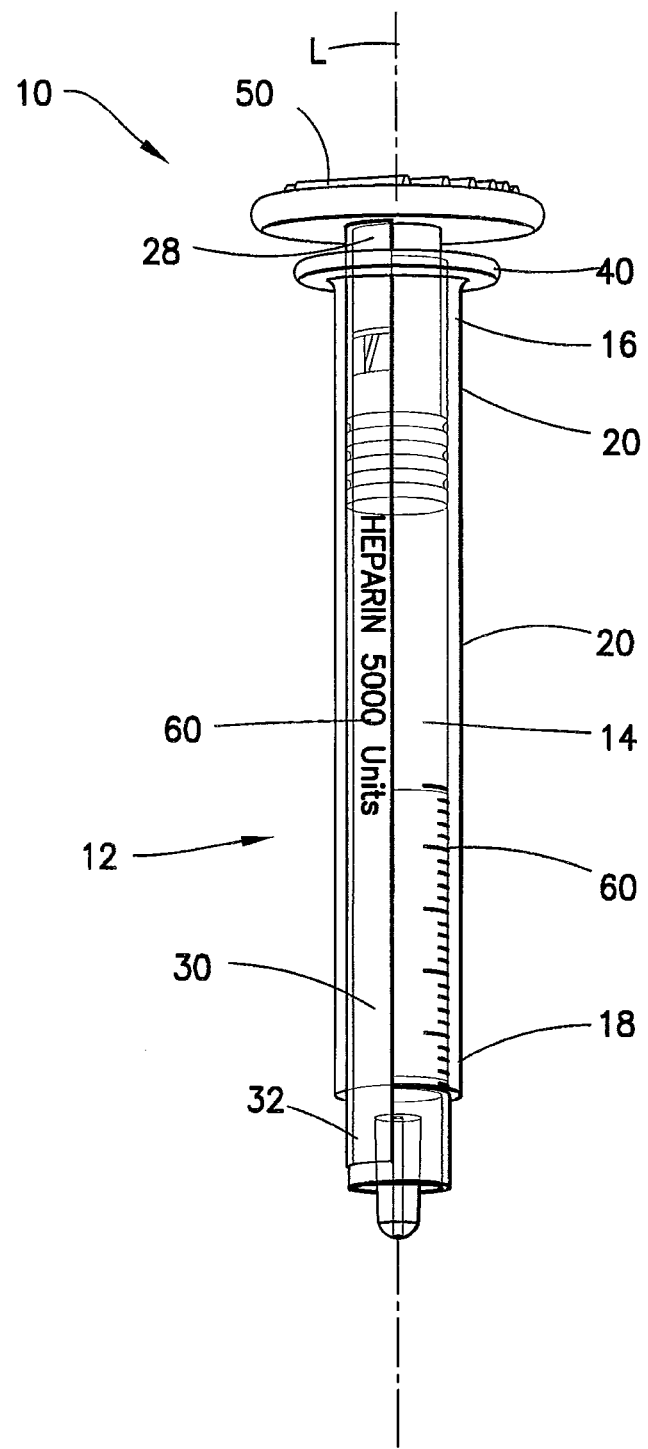
FIG. 1 is a perspective view of a syringe assembly including a collapsed plunger rod having magnification properties according to one design of the invention wherein the plunger rod is in a pre-use position.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Reference is now made to FIG. 1 which shows a syringe assembly, generally indicated as 10, having a collapsed plunger rod with magnification properties, generally indicated as 12, according to one design of the present invention. The syringe assembly 10 includes a syringe barrel 14 with a proximal end 16, a distal end 18, and a sidewall 20 extending between the proximal end 16 and the distal end 18. As shown, the syringe barrel 14 may have a cylindrical or substantially cylindrical shape, though it is to be appreciated that the syringe barrel 14 may be formed in any suitable shape. Additionally, the syringe barrel 14 may be formed of glass, or may be injection molded from thermoplastic material such as polypropylene and polyethylene according to techniques known to those of ordinary skill in the art, though it is to be appreciated that the syringe barrel 14 may be made from other suitable materials and according to other applicable techniques.

Figure 2:
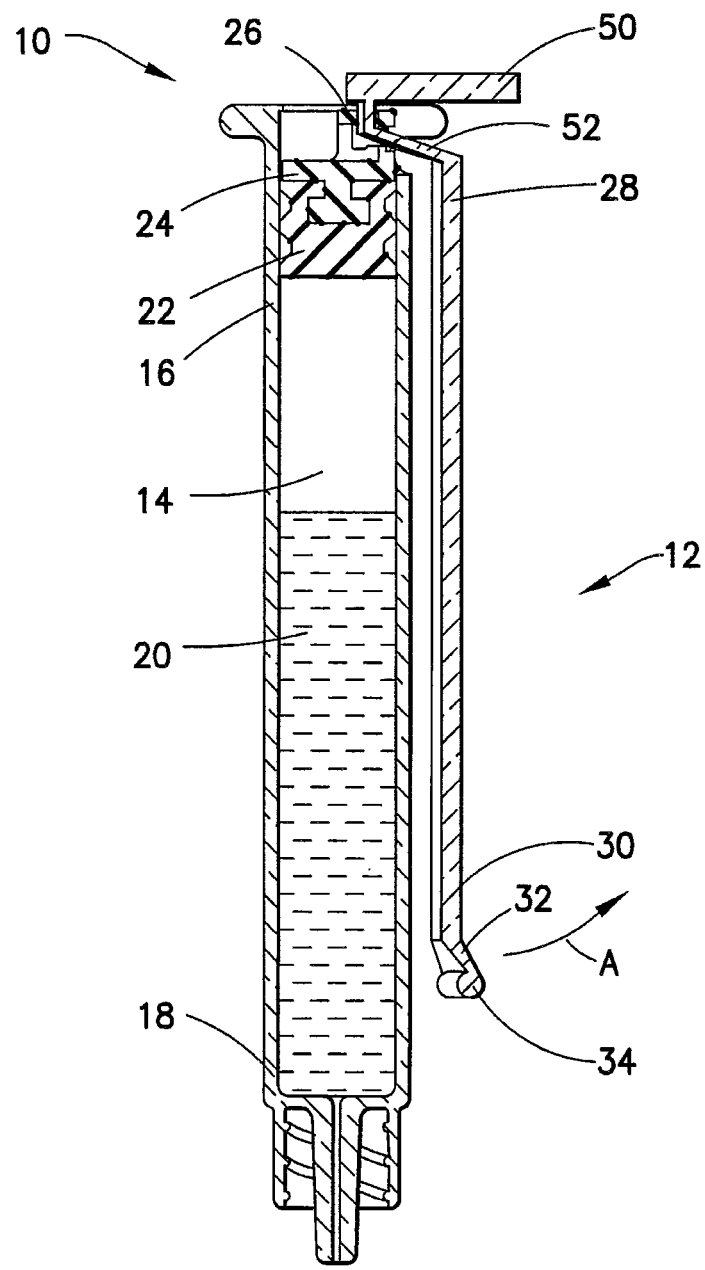
FIG. 2 is a side sectional view of a syringe assembly including the plunger rod having magnification properties according to another design of the present invention wherein the plunger rod is in a pre-use position.

With continuing reference to FIGS. 1-2, a stopper 22 is located within the syringe barrel 14 and a stopper adapter 24 is associated with the stopper 22. The stopper adapter 24 may be integrally formed with the stopper 22 or may be a separately molded member having a first end secured to the stopper 22. The syringe barrel 14, stopper 22, and stopper adapter 24 define a longitudinal axis L, as shown in FIG. 1. The plunger rod 12 may be secured to the stopper adapter 24 and is configured for cooperation with the stopper adapter 24 to move from a collapsed pre-use position to an expanded ready-to-use position. In one embodiment, the plunger rod 12 is adapted to transition from the pre-use position in which the plunger rod 12 extends substantially parallel with the sidewall 20 of the syringe barrel 14, to the expanded ready-to-use position in which the plunger rod 12 extends substantially in line with the longitudinal axis of the syringe barrel 14, stopper 22, and the stopper adapter 24. In one embodiment, the plunger rod 12 includes a first end 28 and a second end 30 with an attachment member 32 disposed adjacent the second end 30. The stopper adapter 24 may include a joining end 26 configured for connection with the attachment member 32 of the plunger rod 12 in the ready-to-use position.

Reference is now made to FIGS. 2-4C which show the syringe assembly having a collapsible plunger rod including magnification properties according to another design of the invention. Like reference numerals are being used for like components of the FIG. 1 design. The syringe assembly 10 includes a containing member 37 adjacent a cut-out portion 46 or recessed groove in the proximal end 16 of the syringe barrel sidewall 20, which is dimensioned to allow a portion of the plunger rod 12 to pass therethrough. The cut-out portion 46 may also be dimensioned such that the first end 28 and the second end 30 may not pass through the cut-out portion 46 and are restrained by the containing member 37 preventing inadvertent separation of the plunger rod 12 from the syringe assembly 10 in the initial pre-use position or during transition of the plunger rod 12 to the ready-to-use position. Outward or pivotal movement by a clinician in the direction of arrow A shown in FIG. 2 can dislodge the plunger rod 12 from the joining end 26 of the stopper adapter 24 for activation of the plunger rod 12 to the expanded ready-to-use state. During transition of the syringe assembly 10 from the initial position to the ready-to-use position, the plunger rod 12 is advanced in an angled substantially proximal direction as shown by arrow A of FIG. 3A.

Figure 3A:
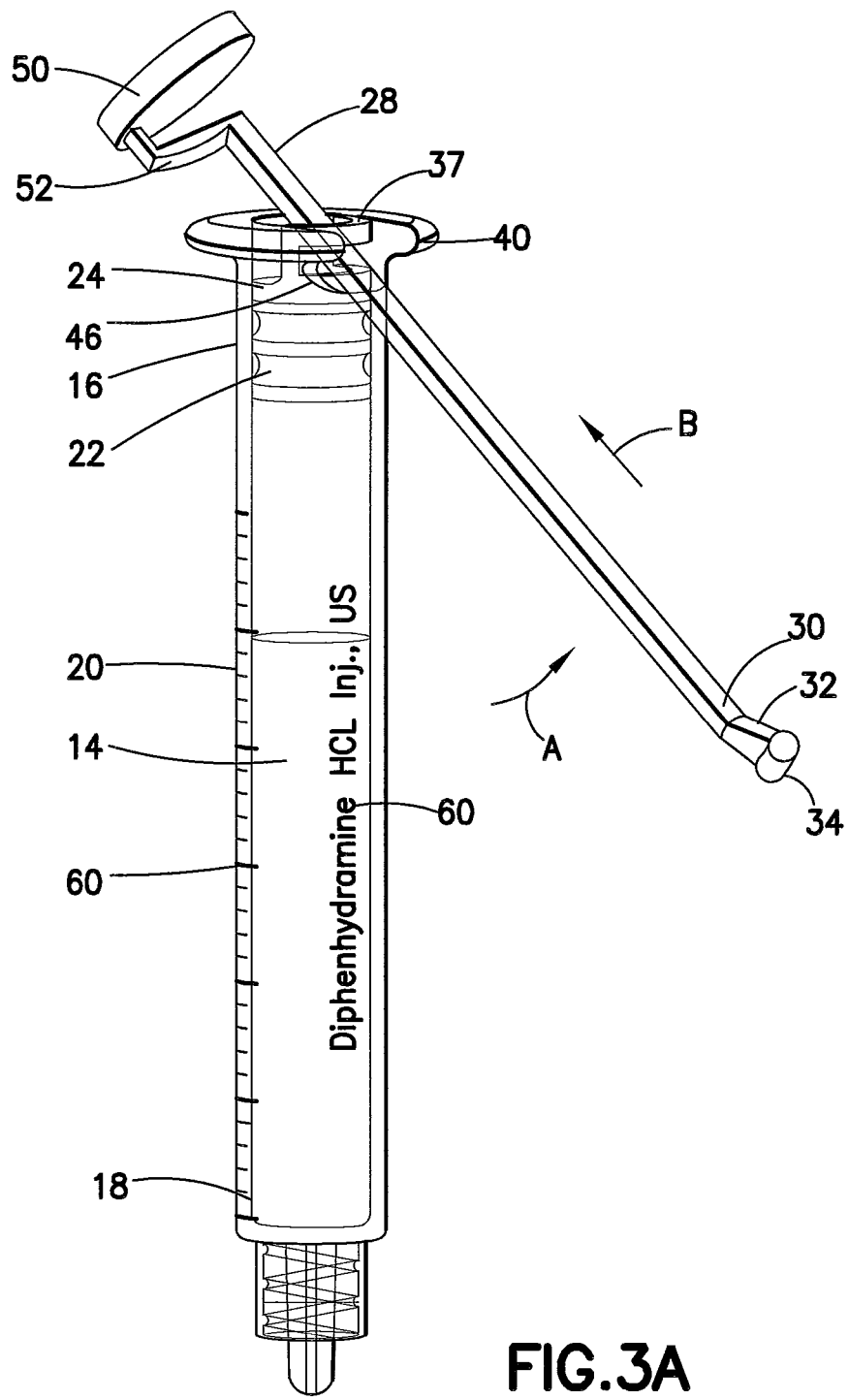
FIG. 3A is a perspective view of a syringe assembly of FIG. 2 having a plunger rod pivoted away from the syringe barrel during transition of the syringe from the initial position to the ready-to-use position.
Figure 3B:
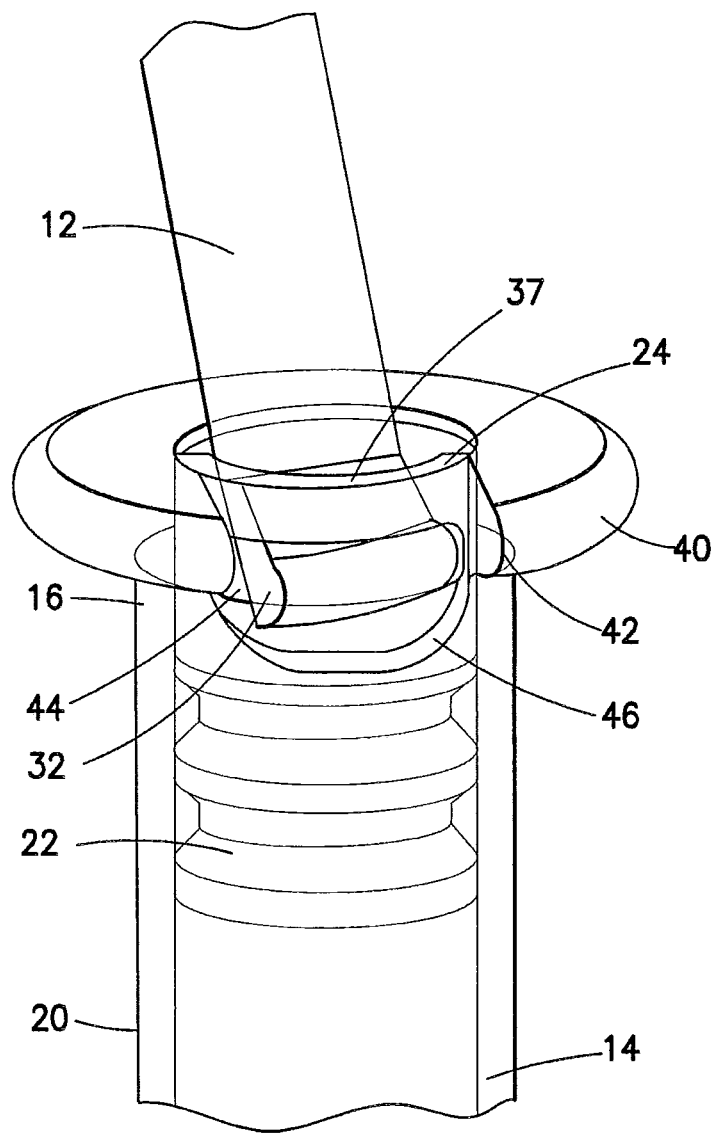
FIG. 3B is a partial perspective view of the syringe assembly of FIG. 3A showing engagement of the plunger rod during transition of the syringe from the initial position to the ready-to-use position.
Figure 3C:
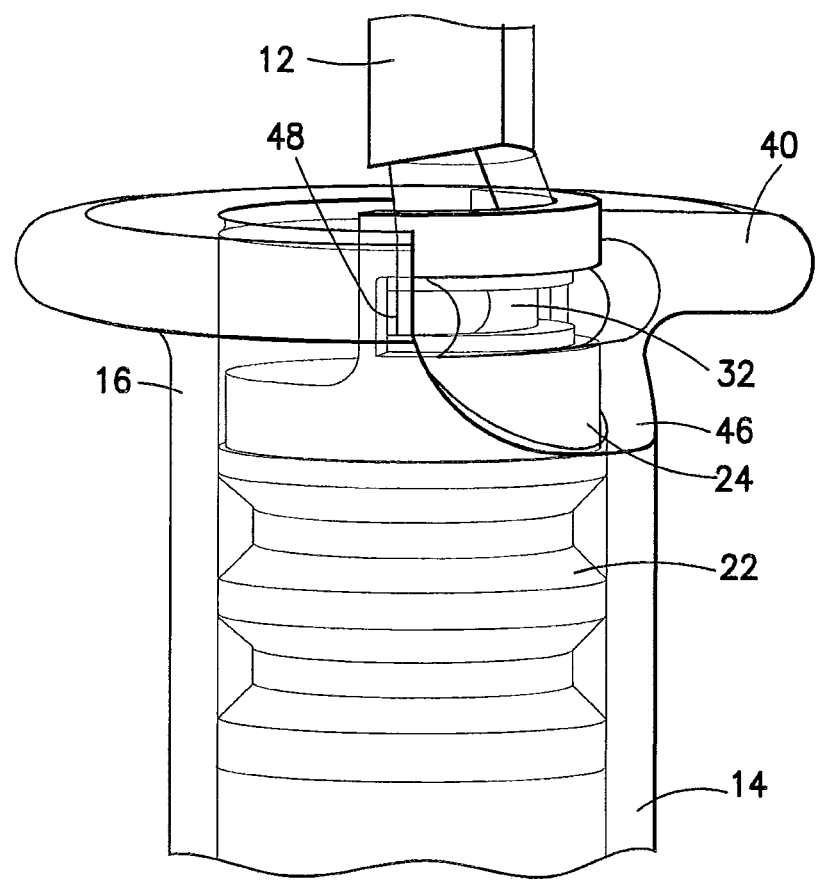
FIG. 3C is a partial perspective view of the syringe assembly of FIG. 3A showing engagement of the plunger rod during further transition of the syringe from the initial position to the ready-to-use position.
Figure 3D:
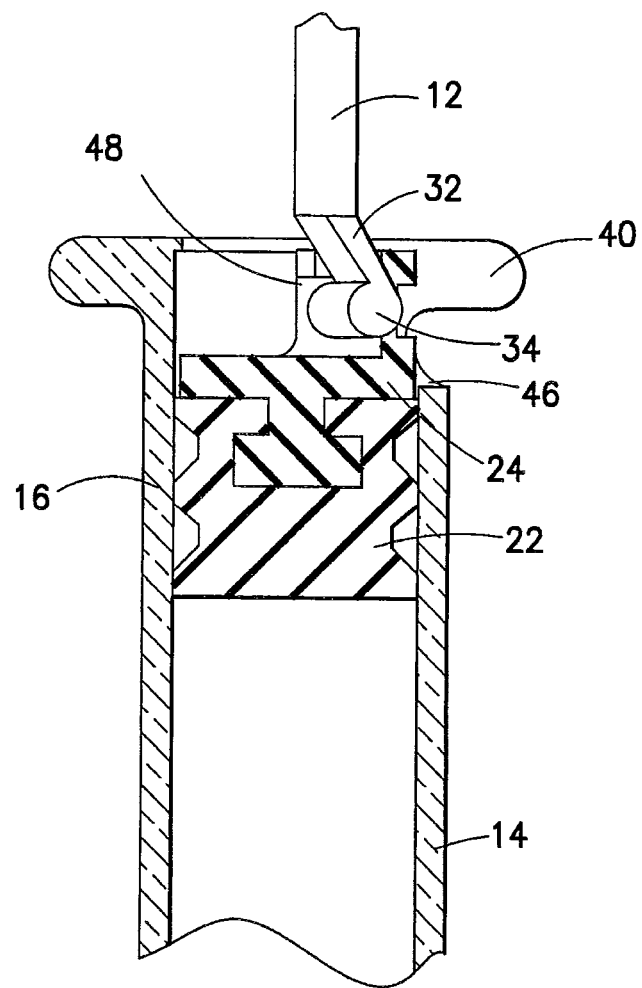
FIG. 3D is a partial front sectional view of the syringe assembly of FIG. 3A in the ready-to-use position.
Figure 4A:
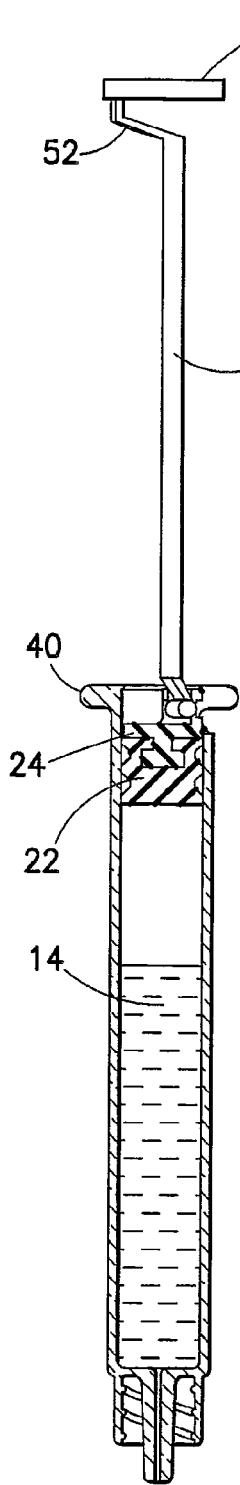
FIG. 4A is a front sectional view of the syringe assembly of FIG. 3A in the ready-to-use position.
Figure 4B:
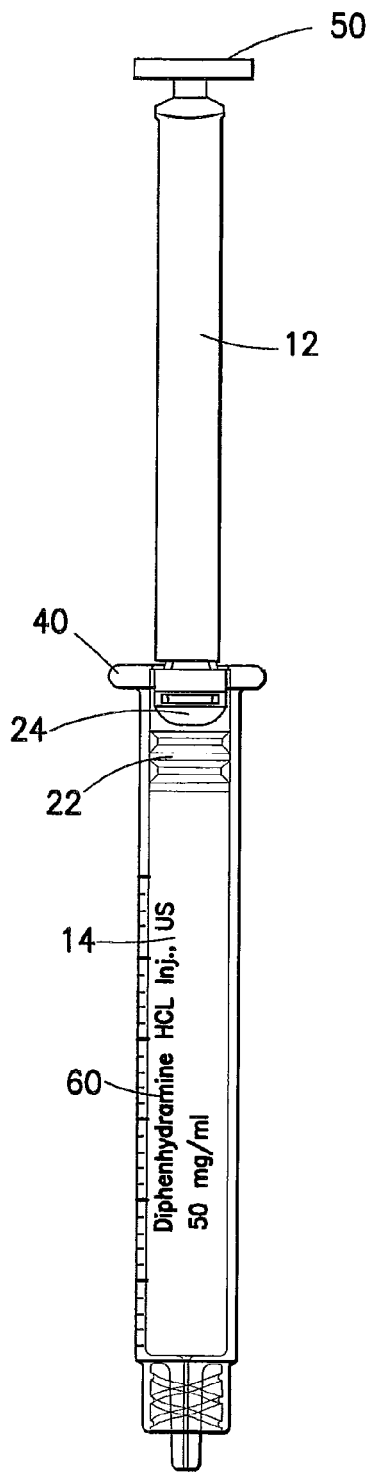
FIG. 4B is a side view of the syringe assembly of FIG. 4A.
Figure 4C:
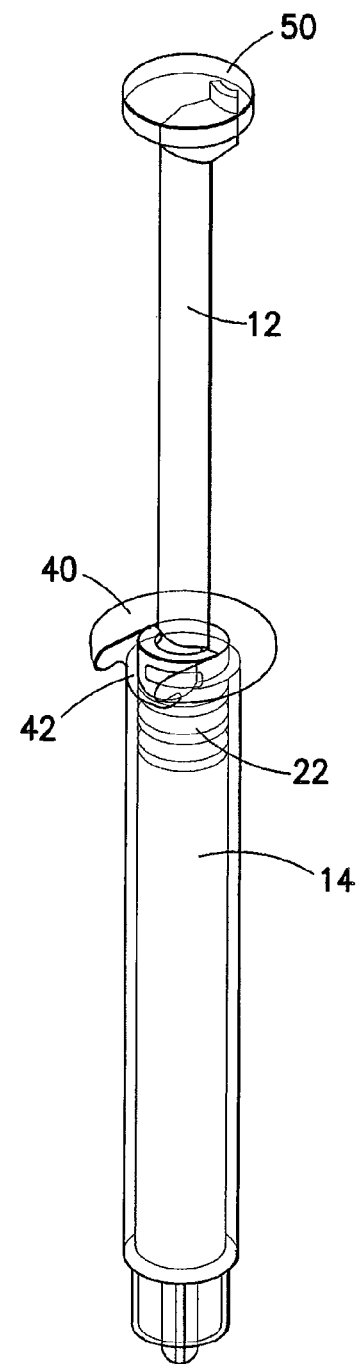
FIG. 4C is a perspective view of the syringe assembly of FIG. 4A.

Reference is now made to FIGS. 3A-3C which shows sequential perspective views of the movement of the collapsed plunger rod 12 into the ready-to-use position. In operation, the plunger rod 12 moves from the collapsed position to the expanded position through a pivoting motion of the second end 30 of the plunger rod 12, as shown in FIG. 3A, in a radial direction with respect to the syringe barrel 14. A subsequent application of a force to the plunger rod 12 in the proximal direction, as shown by arrow B of FIG. 3A causes the plunger rod 12 to slide in an axial direction toward the proximal end 16 of the syringe barrel 14. The syringe assembly 10 can further include a flange 40 located at the proximal end 16 of the syringe barrel 14. This flange 40 can include an opening 42 which is in alignment with an opening 44 in the stopper adapter 24 through which the plunger rod 12 extends. The cut-out portion 46 can be provided in the proximal end 16 of the syringe barrel sidewall 20 to facilitate movement of the attachment member 32 through the flange opening 42 and the stopper adapter opening 44. Openings 42, 44 and cut-out portion 46 are best shown in FIG. 3B. The applied axial movement causes the plunger rod 12 to move through the flange opening 42 and the stopper adapter opening 44 to align the plunger rod 12 along the longitudinal axis of the syringe barrel 14, stopper 22, and stopper adapter 24. The attachment member 32 on the plunger rod 12 can include at least one detent bump 34, as shown in FIG. 2 which then snaps into or connects in any other manner with the joining end 26 of the stopper adapter 24 to secure the plunger rod 12 thereto in the expanded ready-to-use position. The detent bump 34 on the attachment member 32 is joined with a receiving member 48 located in the stopper adapter 24 as is clearly shown in FIGS. 3B and 3D. Optionally, the plunger rod 12 can include a thumb press member 50 located at the first end 28 thereof. Preferably, this thumb press member 50 is located above the proximal end 16 of the syringe barrel 14 and the flange 40. The plunger rod 12 can include an inwardly curved portion 52 to facilitate manipulation of the plunger rod 12 through the openings 42, 44 and the cut-out portion 46 of the syringe barrel 14. The application of force to plunger rod 12 can be applied by a pushing motion to the plunger rod 12 or to the second end 30 of the plunger rod 12 and/or by applying a pulling motion to the thumb press member 50. The transition from the partially expanded position of FIG. 3B to the fully expanded position of FIGS. 3C-3D requires the plunger rod 12 to be slightly moved in a radial direction with respect to the stopper adapter 24 and stopper 22 to snap the attachment member 32 into the receiving member 48 of the stopper adapter 24 so that the plunger rod 12 is axially aligned with the longitudinal axis of the syringe barrel 14, stopper adapter 24, and stopper 22, placing the syringe assembly 10 in the ready-to-use position. The syringe assembly 10 is shown in FIGS. 4A-4C in the ready-to-use position having the plunger rod 12 fully extended and engaged with the stopper adapter 24. It can be appreciated that the thumb press can be made sufficiently rigid to ensure that when pressed, the force from this press will translate into movement purely in an axial direction.

Figure 5:
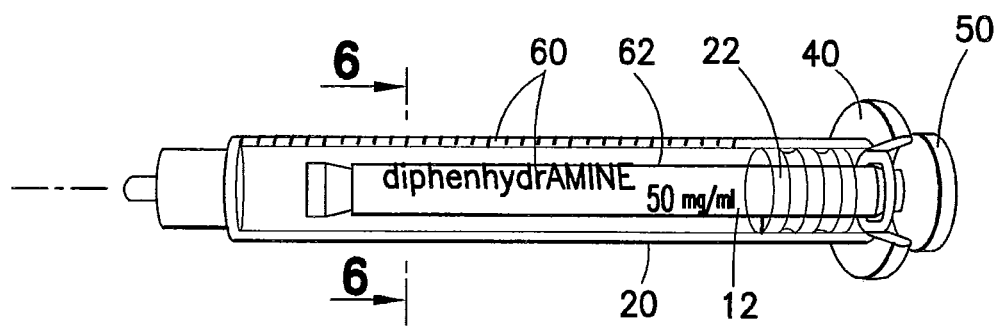
FIG. 5 is a perspective view of a syringe assembly having a collapsed plunger rod having magnification properties in an initial position.
Figure 6:
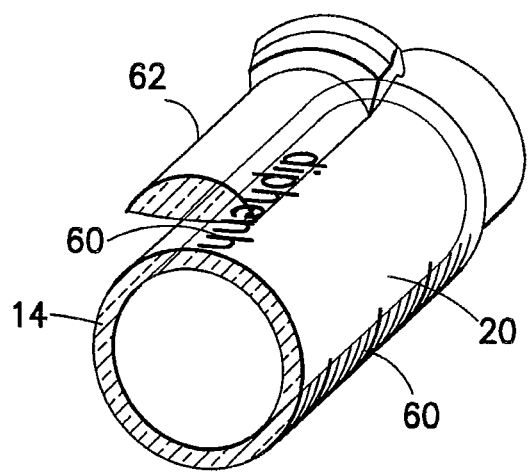
FIG. 6 is a partial cross-sectional view of the syringe assembly of FIG. 5 taken along line 6-6.

With continuing reference to FIGS. 1-4D, and with reference to FIGS. 5 and 6, the syringe assembly 10 further includes a magnification member, shown as reference number 62 in FIGS. 5-6, for magnifying any indicia 60 located on the syringe barrel sidewall 20. The syringe barrel sidewall 20 can include indicia 60 printed directly thereon or printed on a label secured to the barrel sidewall 20. This indicia 60 can include label information such as the drug name, concentration, expiration, and the like. The indicia 60 can also include dosing information or barrel markings. In one embodiment, the magnification member 62 is provided in pivotal relation with a portion of the stopper 22 and/or stopper adapter 24 in the initial position such that the magnification member 62, or plunger rod 12 having a magnification region disposed thereon, may be rotated about the syringe barrel sidewall 20 prior to transitioning the plunger rod 12 to the ready-to-use position. One modification to this embodiment can include a plunger rod 12 having a separate magnification region co-formed therewith.

In one embodiment, the magnification member 62 of the invention can magnify the indicia 60 up to about 1½ times its size, allowing for easier viewing of dosing information and/or contents information which may result in a reduction in medication error. In another embodiment, the magnification member 62 of the invention can magnify the indicia 60 more than 1½ times its size. By changing the spacing between the plunger rod 12 and the barrel sidewall 20 or label, or by altering the curvature of the barrel sidewall 20, varying levels of magnification can be achieved.

Figure 7A:
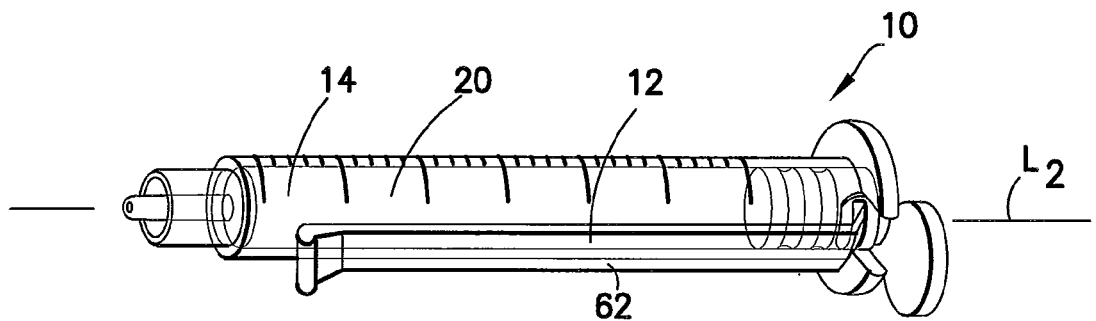
FIG. 7A is a perspective view of a syringe assembly having a plunger rod having magnification properties according to yet another design of the present invention wherein the plunger rod is in an initial position.
Figure 7B:
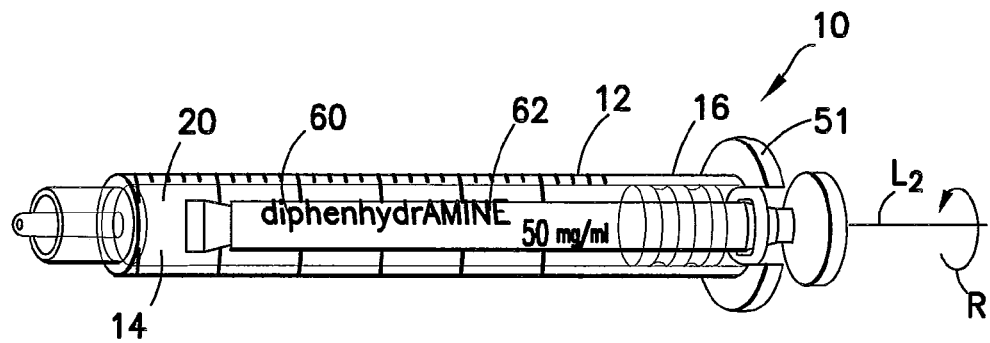
FIG. 7B is a perspective view of the syringe assembly of FIG. 7A having the plunger rod having magnification properties rotated over indicia disposed in the syringe barrel.
Figure 7C:
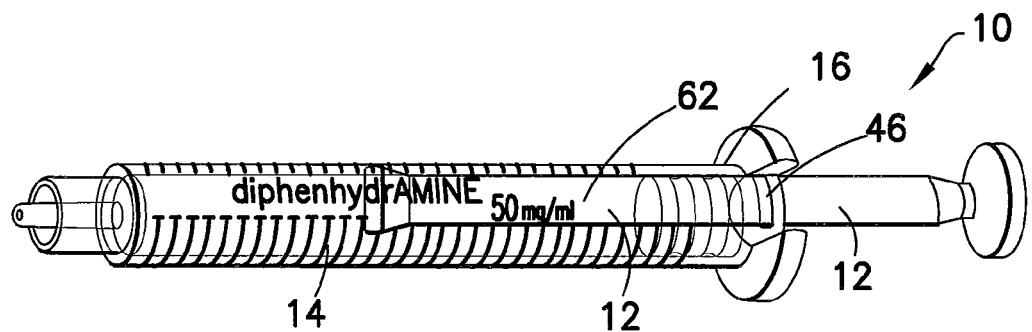
FIG. 7C is a perspective view of the syringe assembly of FIG. 7A having the plunger rod rotationally and partially axially advanced.
Figure 7D:
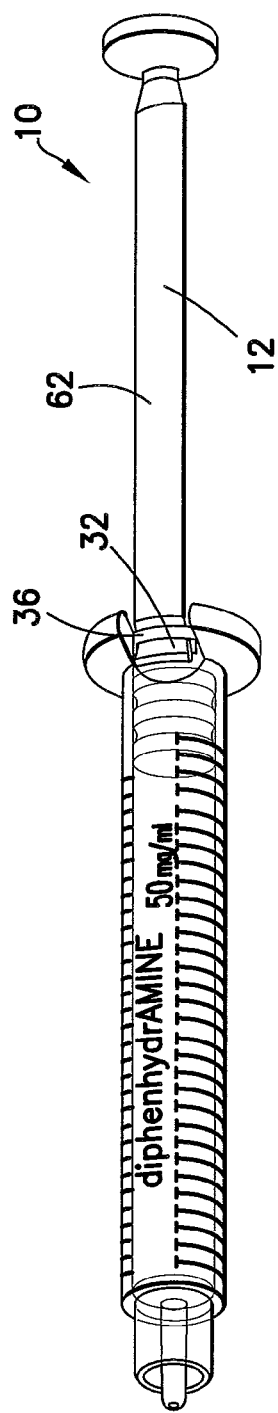
FIG. 7D is a perspective view of the syringe assembly of FIG. 7A having the plunger rod fully extended.
Figure 7E:
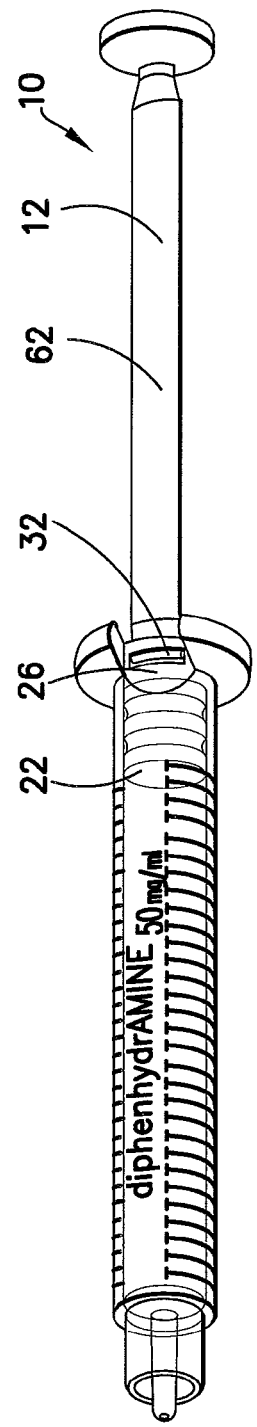
FIG. 7E is a perspective view of the syringe assembly of FIG. 7A in the ready-to-use position.
Figure 7F:
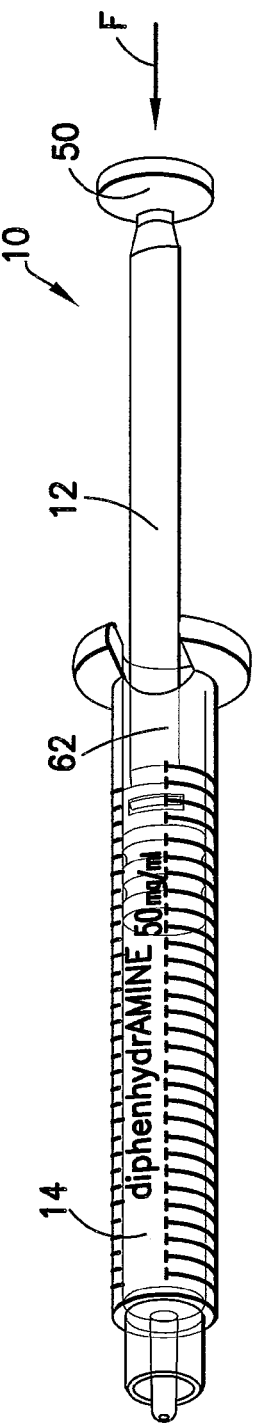
FIG. 7F is a perspective view of the syringe assembly of FIG. 7A having the plunger rod partially deployed to expel contents of the syringe barrel.

Referring to FIGS. 7A-7F, showing yet another design of the collapsible plunger rod of the invention, the usage of a syringe assembly 10 having a collapsible plunger rod 12 having a magnification member 62 is shown. The syringe assembly 10 is shown in its initial unused position in FIG. 7A. It can be appreciated that the syringe assembly can be designed such that the proximal end 16 of the syringe includes a snap ring 51 as a separately attached item. In this design, with reference to FIG. 7B, the snap ring 51 on the proximal end 16 of the syringe body could be removed which would allow the plunger rod 12 having a magnification member 62, along with the stopper 22 and the stopper adapter 24 to rotate as a unit about the longitudinal axis $L_2$ of the syringe barrel 14 in the direction shown by arrow R. As such, the magnification member 62 of the plunger rod 12 may be rotated over indicia 60 disposed on or with the syringe barrel sidewall 20, allowing a medical practitioner to easily identify the contents and dosing of the syringe assembly 10 prior to use. As shown in FIG. 7C, the plunger rod 12 may be pivoted away from the syringe barrel sidewall 20, as shown by arrow A of FIGS. 2-3A, and pulled axially toward the proximal end 16 of the syringe barrel 14, as shown by arrow B of FIG. 3A, through cut-out portion 46. The fully extended plunger rod 12 is shown in FIG. 7D, having the attachment member 32 restrained by the containing member 37 to prevent separation of the plunger rod 12 from the syringe assembly 10. As shown in FIG. 7E, the attachment member 32 is engaged with the second end 26 of the stopper adapter 24 to secure the plunger rod 12 with the stopper 22. As shown in FIG. 7F, the plunger rod 12 may be then deployed to expel the contents of the syringe barrel 14 by providing an axial force in the direction shown by arrow F to the thumb press member 50.

Figure 8:
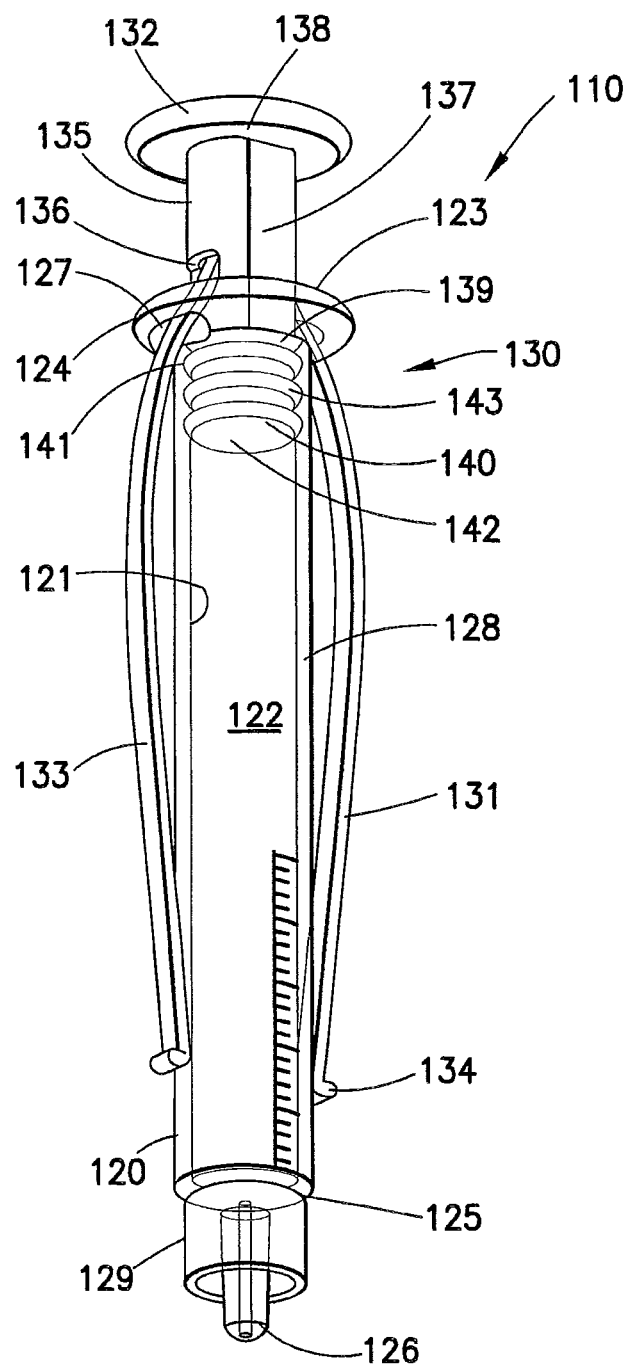
FIG. 8 is a perspective view of a syringe assembly having magnification properties according to another embodiment of the invention.

According to another embodiment, FIG. 8 shows one type of syringe assembly 110 having multiple legs 131, 133 wherein one or more of the legs include magnification properties. In particular, the syringe assembly 110 includes a syringe barrel 120 and a plunger assembly 130. The syringe barrel 120 has an open proximal end 123 and a distal end 125 opposite to the open proximal end 123. The syringe barrel 120 has an inside surface 121, which defines a chamber 122. The syringe barrel 120 also includes a substantially conical outlet tip 126 disposed on the distal end 125 of the syringe barrel 120 in the form of a conventional luer fitting. The outlet tip 126 is in fluid communication with the chamber 122 of the syringe barrel 120. A needle cannula (not shown) may be attached to the outlet tip 126 such that an interior of the needle cannula is in fluid communication with the chamber 122 of the syringe barrel 120. The needle cannula may be secured within the outlet tip 126 by a chemical adhesive, such as epoxy, or may be mechanically affixed to the outlet tip 126 according to known techniques. Alternatively, syringe assembly 110 is contemplated for use in connection with a separate needle assembly (not shown) such as through a standard luer slip fitting or luer lock fitting type connection with syringe assembly 110 at the outlet tip 126, or alternatively to a separate intravenous (IV) connection assembly (not shown). As such, a threaded luer collar 129 may further be provided for threaded engagement with such a separate mechanism, as is known in the art.

The syringe assembly 110 may also include a protective cap (not shown) disposed over the outlet tip 126 to protect the needle cannula prior to use and to prevent accidental needle sticks of persons handling the syringe assembly 110 prior to use. An annular ridge (not shown) may be formed on the distal end 125 of the syringe barrel 120 to facilitate attachment of a protective cap or a standard needle hub over the outlet tip 126. An outwardly extending flange 124 may also be provided at the proximal end 123 of the syringe barrel 120 to assist in handling of the syringe assembly 110. The outwardly extending flange 124 may have a pair of opposing apertures 127 extending through the flange 124.

With further reference to FIG. 8, the syringe assembly 110 also includes a plunger assembly 130 disposed at least partially within the syringe barrel 120. The plunger assembly 130 includes a handle portion 132 at the proximal end of the plunger assembly 130 and a pair of flexible legs 131, 133 extending distally from the handle portion 132. The flexible legs 131, 133 each have a hook 134 formed at their distal ends. The plunger assembly 130 also includes a plunger head in the form of stopper 140 disposed within the chamber 122 of the syringe barrel 120. The stopper 140 includes a proximal surface 141, a distal surface 142, and a peripheral surface 143 extending between the proximal 141 and distal 142 surfaces. The peripheral surface 143 of the stopper 140 includes one or more sealing surfaces, such as an annular rib, so that the stopper 140 engages the inside surface 121 of the syringe barrel 120 so as to seal the chamber 122.

A stopper adapter 135 is formed as an at least partially hollow cylindrical member having a sidewall 137 extending between a proximal end 138 and a distal end 139. The distal end 139 of the stopper adapter 135 is attached to the proximal surface 141 of the stopper 140. A pair of slots 136 is formed in the sidewall 137 of the stopper adapter 135 so that the flexible legs 131, 133 of the plunger assembly 130 may pass through the stopper adapter 135 from the proximal end 138 of the plunger rod and through the sidewall 137 via the slots 136 during use in an injection cycle.

In the initial position illustrated in FIG. 8, the plunger assembly 130 is in a collapsed position with the flexible legs 131, 133 extending through the slots 136 in the sidewall 137 of the stopper adapter 135 as well as the apertures 127 in the outwardly extending flange 124 and alongside and adjacent to an exterior surface 128 of the syringe barrel 120 to wrap over or around the exterior surface 128 of the syringe barrel 120 with the handle portion 132 of the plunger assembly 130 positioned proximate to the proximal end 123 of the syringe barrel 120, which minimizes the overall length of the syringe assembly 110. It can be appreciated that the thumb press can be made sufficiently rigid to ensure that when pressed, the force from this press will translate into movement purely in an axial direction. Either of both of the flexible legs 131, 133 can be provided with magnification properties so that one can readily view any indicia on the syringe barrel 120. It can be appreciated that magnification properties can be bestowed on other types of multiple leg collapsible plunger rod assemblies which are not explicitly shown herein.

Figure 9:
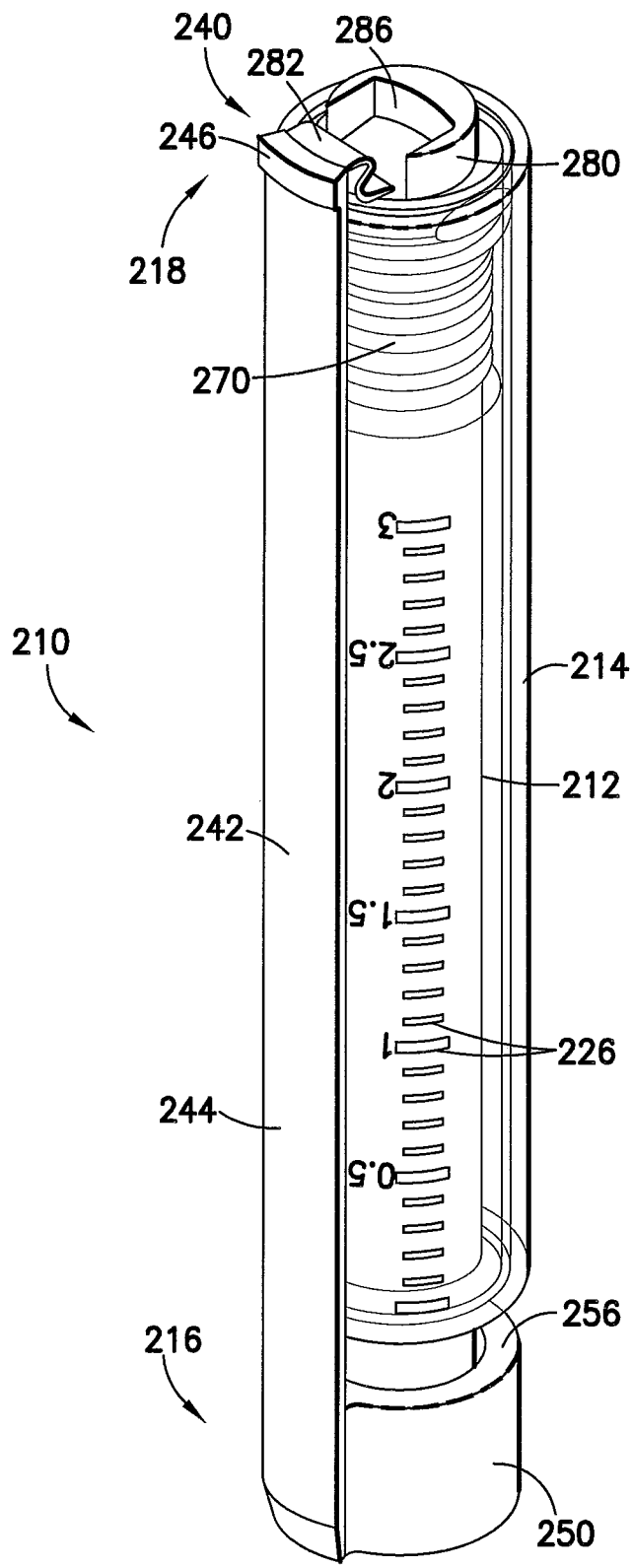
FIG. 9 is a perspective view of a syringe assembly having magnification properties according to yet another embodiment of the invention.

According to yet another embodiment, FIG. 9 shows a syringe assembly, generally indicated as 210, having a pivoting plunger and integral tip guard wherein the pivoting plunger includes magnification properties. The syringe assembly 210 includes a syringe barrel 212 defined by barrel wall 214 extending between a forward or distal end 216 and a rearward or proximal end 218, thereby defining interior chamber of syringe barrel 212. Syringe barrel 212 may include markings, such as graduations 226 on the wall thereof or medication or dosing indicia or other identifying information, as may be known in the art.

The syringe assembly 210 further includes a plunger assembly 240, a portion of which is adapted to be disposed at least partially within syringe barrel 212. Plunger assembly 240 provides a mechanism for dispensing fluid contained within the interior chamber of syringe barrel 212. In particular, plunger assembly 240 includes a plunger rod 242, which provides a mechanism for extension of a stopper portion such as plunger head 270 disposed within interior chamber for dispensing the contents of the syringe assembly 210.

Plunger rod 242 is a generally elongated structure extending between first end 244 and second end 246. Plunger rod 242 is adapted for positioning adjacent along the outside of wall 214 of syringe barrel 212 with first end 244 adjacent forward end 216 of syringe barrel 212 in a first position, and is further adapted for pivotal movement to a second position with first end 244 extending axially beyond rearward end 218 of syringe barrel 212 with the elongated structure of plunger rod 242 in general axial alignment with syringe barrel 212 at rearward end 218 thereof. Plunger rod 242 may further include magnification properties which may be disposed along the elongated portion of plunger rod 242 so as to magnify the markings, such as graduations 226, on the wall of syringe barrel 212 or any other type of identifying indicia when plunger rod 242 is positioned along the outside of wall 214 of syringe barrel 212, allowing a user to more easily identify the volume of liquid contained in syringe barrel 212 before or after use.

First end 244 of plunger rod 242 may be provided with a mechanism for engagement with outlet opening of syringe barrel 212 for maintaining sterility thereof. For example, a cap such as tip guard 250 may be provided at first end 244. Tip guard 250 may be integrally formed with plunger rod 242, or may be a separate structure that is attached to first end 244 of plunger rod 242. Tip guard 250 further includes an annular skirt 256 forming a cylindrical opening therein. The cylindrical opening includes an inner diameter that is substantially the same as the outer diameter of the annular skirt formed by a luer lock, and is adapted to surround the luer lock in a sealing engagement.

The second end 246 of plunger rod 242 is adapted for interconnection with plunger head 270. Plunger head 270 is adapted for movement within the interior chamber of syringe barrel 212.

The interconnection between plunger head 270 and plunger rod 242 at second end 246 thereof provides for pivoting movement of plunger rod 242 with respect to plunger head 270. In one embodiment, syringe assembly 210 may further be provided with a connector 280 for interconnecting second end 246 of plunger rod 242 with plunger head 270. Connector 280 further includes a recessed profile 286 on an external surface thereof for accommodating second end 246 of plunger rod 242 when plunger rod 242 is pivoted to the second position to be in axial alignment with syringe barrel 212. It can be appreciated that magnification properties can be bestowed on other types of pivoting plunger/integral tip guard plunger rod assemblies which are not explicitly shown herein.

Figure 10:
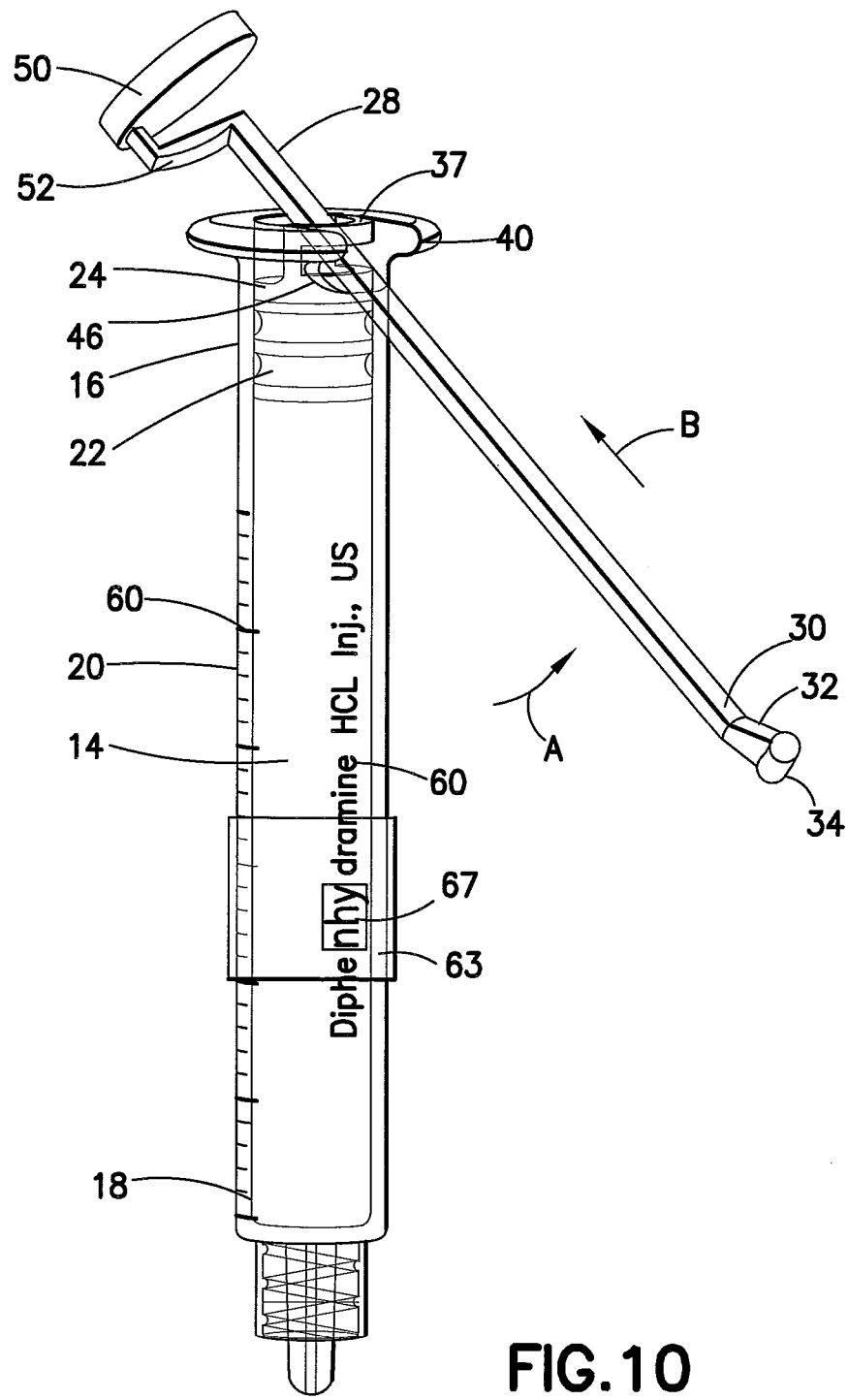
FIG. 10 is a perspective view of the syringe assembly having magnification properties according to still another embodiment of the invention.

FIG. 10 shows still another embodiment wherein the magnification member can be a substantially cylindrical sleeve 63 circumferentially disposed about the syringe barrel 14. This sleeve can include a magnification lens 67 incorporated therein. In another embodiment, the magnification member can be a separate element having a mating engagement with a substantially cylindrical sleeve. In yet another embodiment, the magnification member can be a separate element having a mating engagement with a portion of a label disposed on a portion of the barrel sidewall 20.

Although the invention has been described in terms of the plunger rod having magnification properties, it can be appreciated that the plunger rod can be designed such that it decreases the magnification of indicia located on a syringe barrel.

It can be appreciated that the collapsible plunger rod of the invention locks in place during use and then is contained within the syringe body after use, to reduce the length of the syringe assembly to allow for sharps disposal. The use of the syringe assembly 10 having a collapsed plunger rod 12 of the invention can result in up to approximately a 70% reduction in length of the packaged syringe product.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention.

The invention claimed is:

1. A syringe assembly having a collapsed plunger rod comprising:
   a syringe barrel having a proximal end, a distal end, and a sidewall extending between the proximal end and the distal end;
   a stopper located within the syringe barrel;
   a stopper adapter associated with said stopper wherein said syringe barrel, said stopper, and said stopper adapter define a longitudinal axis; and
   the plunger rod extending through said stopper adapter in a collapsed pre-use position and configured for cooperation with said stopper adapter to move from the collapsed pre-use position, where the plunger rod extends substantially parallel with the syringe barrel sidewall, to an expanded ready-to-use position where the plunger rod extends substantially in line with the longitudinal axis of the syringe barrel, the stopper, and the stopper adapter, wherein the plunger rod includes a first end and a second end whereby the second end is located adjacent the distal end of the syringe barrel when said plunger rod is in the collapsed pre-use position and said second end of said plunger rod is configured to secure the plunger rod to the stopper adapter in the expanded ready-to-use position;
   wherein said plunger rod comprises a magnification member for magnifying any indicia located on the syringe barrel when the plunger rod is positioned in the collapsed pre-use position.

2. The syringe assembly of claim 1, wherein the second end of the plunger rod includes an attachment member for securing the plunger rod to the stopper adapter in the expanded ready-to-use position.

3. The syringe assembly of claim 2, including a flange located at the proximal end of the syringe barrel, said flange including an opening in alignment with an opening in the stopper adapter through which the plunger rod extends wherein movement of the plunger rod from the collapsed pre-use position to the expanded ready-to-use position includes pivoting the second end of the plunger rod in a radial direction with respect to the syringe barrel and then applying a proximal force to the plunger rod to axially slide the plunger rod through the openings in the flange and the stopper adapter and secure the attachment member on the second end of the plunger rod with the stopper adapter.

4. The syringe assembly of claim 2 wherein the plunger rod includes a thumb press member located at said first end of said plunger rod and is located above the proximal end of the syringe barrel.

5. The syringe assembly of claim 2 wherein the plunger rod remains secured to the syringe assembly during movement from the collapsed pre-use position to the expanded ready-to-use position.

6. The syringe assembly of claim 1, wherein said plunger rod, said stopper, and said stopper adapter are configured for rotational movement with respect to the syringe barrel.

7. A syringe assembly comprising:
   a syringe barrel having an exterior surface, an inside surface defining a chamber, an open proximal end, a distal end, and an outlet disposed adjacent the distal end in fluid communication with the chamber; and
   a plunger assembly disposed at least partially within the syringe barrel, the plunger assembly including an elongated plunger rod and a plunger head, the elongated plunger rod being associated with the plunger head to move the plunger head within the chamber of the syringe barrel through an injection cycle;

wherein the elongated plunger rod is adapted to move from a collapsed position extending alongside the exterior surface of the syringe barrel to an extended position engaging the plunger head to move the plunger head through the injection cycle, wherein the plunger rod includes a first end and a second end whereby the second end is located adjacent the distal end of the syringe barrel when said plunger rod is in the collapsed position and said second end of said plunger rod is configured to secure the plunger rod to the plunger head in the extended position, wherein movement from the collapsed position to the extended position includes pivoting the second end of the plunger rod in a radial direction with respect to the syringe barrel and then applying a proximal force to the elongated plunger rod to position the plunger rod in the extended position, and wherein the plunger rod comprises a magnification member for magnifying indicia located on the syringe barrel when the plunger rod is positioned in the collapsed position.

8. A syringe assembly having magnification properties comprising:

a syringe barrel having a proximal end, a distal end, and a sidewall extending between the proximal end and the distal end, said sidewall including indicia located thereon;

a plunger rod associated with the syringe barrel, said plunger rod having a first end including a thumb press member associated therewith; and a magnification member associated with the syringe barrel sidewall for magnifying said indicia, wherein the magnification member comprises the plunger rod and magnification of said indicia occurs when the plunger rod is in a collapsed position having at least a portion thereof positioned adjacent the syringe barrel sidewall and said thumb press member is located above the proximal end of the syringe barrel, and wherein movement of the plunger rod from the collapsed position to an extended engagement position includes pivoting a second end of the plunger rod in a radial direction with respect to the syringe barrel and then applying a proximal force to the plunger rod to position the plunger rod in the extended engagement position.

9. The syringe assembly of claim 8, wherein said plunger rod is rotatably attached to the syringe assembly to allow for rotational movement of the plunger rod with respect to said syringe barrel sidewall to align the plunger rod with the indicia.

10. The syringe assembly of claim 8, wherein the indicia is either printed on a label and secured to the syringe barrel sidewall, or the indicia is printed directly on the syringe barrel sidewall.

11. The syringe assembly of claim 8, wherein the magnification member comprises a separate element having a mating engagement with the plunger rod.

12. A syringe assembly, comprising:

a syringe barrel having an inside surface defining a chamber, an open proximal end, and a distal end having an opening therethrough;

an elongated plunger rod extending between a first end and a second end, said plunger rod comprising a magnification member; and a plunger head extending within the chamber of the syringe barrel, the second end of the plunger rod interconnected with the plunger head through a pivotable connection, wherein the plunger head is adapted for slidable movement within the syringe barrel between the proximal end and the distal end, wherein the plunger rod is adapted to pivot with respect to the plunger head between a first position in which the plunger rod is adjacent the syringe barrel and the second end of the plunger rod is positioned adjacent the distal end of the syringe barrel, and a second position in which the second end of the plunger rod is associated with the plunger head and the plunger rod is in general axial alignment with the syringe barrel, and is further adapted for axial movement so as to cause said slidable movement of the plunger head through the syringe barrel, wherein movement of the plunger rod from the first position to the second position includes pivoting the second end of the plunger rod in a radial direction with respect to the syringe barrel and then applying a proximal force to the plunger rod, and wherein the magnification member magnifies indicia located on the syringe barrel when the plunger rod is located at the first position.

13. A syringe assembly having a collapsed plunger rod comprising:

a syringe barrel having a proximal end, a distal end, and a sidewall extending between the proximal end and the distal end;

a stopper located within the syringe barrel;

a stopper adapter associated with said stopper wherein said syringe barrel, said stopper, and said stopper adapter define a longitudinal axis; and the plunger rod extends through said stopper adapter in a collapsed pre-use position and is configured for cooperation with said stopper adapter to move from the collapsed pre-use position, where the plunger rod extends substantially parallel with the syringe barrel sidewall, to an expanded ready-to-use position where the plunger rod extends substantially in line with the longitudinal axis of the syringe barrel, the stopper, and the stopper adapter, wherein the plunger rod includes a first end and a second end, said second end being located adjacent the distal end of the syringe barrel when said plunger rod is in the collapsed pre-use position, wherein the plunger rod includes a thumb press member located at said first end of said plunger rod and is located above the proximal end of the syringe barrel, and wherein said plunger rod comprises a magnification member for magnifying any indicia located on the syringe barrel when the plunger rod is positioned in the collapsed pre-use position.

14. The syringe assembly of claim 13, wherein movement of the plunger rod from the collapsed pre-use position to the expanded ready-to-use position includes pivoting the second end of the plunger rod in a radial direction with respect to the syringe barrel and then applying a proximal force to the plunger rod to axially slide the plunger rod with respect to the syringe barrel.

* * * * *